United States Patent [19]
Nappholz

[11] Patent Number: 5,792,197
[45] Date of Patent: Aug. 11, 1998

[54] IMPLANTED CARDIAC DEVICE WITH MEANS FOR CLASSIFYING PATIENT CONDITION

[76] Inventor: Tibor A. Nappholz, 8524 E. Jamison Ave., Englewood, Colo. 80112

[21] Appl. No.: 842,740

[22] Filed: Apr. 16, 1997

Related U.S. Application Data

[60] Provisional application No. 60/016,485 Apr. 29, 1996.
[51] Int. Cl.⁶ .................................................. A61N 1/365
[52] U.S. Cl. ........................................................ 607/17
[58] Field of Search ........................ 607/17, 18, 19, 607/20, 21, 22, 23, 24, 25, 4; 600/509, 510, 508

[56] References Cited

U.S. PATENT DOCUMENTS

| | | | |
|---|---|---|---|
| 4,960,129 | 10/1990 | DePaola et al. | 600/508 |
| 5,161,527 | 11/1992 | Nappholz et al. | 607/4 |
| 5,188,106 | 2/1993 | Nappholz et al. | 607/24 |

*Primary Examiner*—Scott M. Getzow
*Attorney, Agent, or Firm*—Gottlieb, Rackman & Reisman

[57] ABSTRACT

An implantable rate responsive pacemaker uses the physiological demand parameter to determine the classification of the patient (i.e., his degree of congestive heart failure). For this purpose, the parameter is monitored for extended time periods (i.e., several days) to determine the levels for said parameter corresponding to different levels of physical activity, such as maximum physical activity or rest. The variation in these levels is then translated into corresponding classification (0-IV) using a preselected criteria.

21 Claims, 3 Drawing Sheets

IMPLANTED CARDIAC DEVICE WITH MEANS FOR CLASSIFYING PATIENT CONDITION

This application claims the benefit of Provisional Application No. 60/016,485 filed Apr. 29, 1996.

BACKGROUND OF THE INVENTION

A. Field of Invention

This invention pertains to a cardiac implant wherein a metabolic demand parameter, and more particularly, long term variations in this parameter, are used to classify the cardiac condition of the patient into one of five categories, said categories being defined by the New York Heart Association.

B. Background of the Invention

In the early days, pacemakers and defibrillators were implanted only for patients with chronic heart disease. Moreover, implanting these devices was thought to be a major, complicated procedure. In recent times, however, the cost of these devices has dropped and the clinicians are performing their implantation so often that the procedure has become routine, rather than a complicated risky procedure. One result of this has been that today a pacemaker or defibrillator device may be frequently used as a precaution even if the patient does exhibit signs of mere cardiac rhythm irregularity which is much less severe than chronic heart disease.

Cardiac patients are classified as belonging as one of five classes rated in increasing severity from 0 to 4 based on specific criteria set forth by the New York Heart Association. This classification is normally based on the ability of a patient to do certain types of exercise, and is related to the maximum oxygen consumption of the patient during said exercises. The standard method of obtaining data for classifying a patient therefore is to have the patient perform various exercises at the clinician's office. The clinician monitors various metabolic functions of the patient during these exercises, such as, for example, his oxygen consumption. After the exercise is completed, the physician assigns a classification for the patient, based on standard statistical information for the patient and his sex, weight, age, and so on, with "0" indicating a healthy patient, "1" indicating a mildly impaired patient, and so on. Thus, a patient is placed one of class 0–4. A disadvantage of this old approach is that it can be performed only in a hospital, or a clinician's office, to the inconvenience of the patient.

A further problem with present classifying means and method is that the peak oxygen consumption for Class 0 and Class 1 patients is very close and therefore it is difficult to differentiate between these two conditions reliably and accurately.

The present invention discloses a method and apparatus which uses a metabolic parameter monitored by an implanted pacemaker to perform the cardiac classification of the patient. By this means, the classification can be performed and updated automatically without the clinician being present and without the patient being in the clinician's office. Moreover, the classification may be used in the pacemaker itself to alter its programming.

OBJECTIVES AND SUMMARY OF THE INVENTION

An objective of the present invention is to provide a pacemaker in which a metabolic demand parameter is used as an indicia of cardiac condition of a patient.

A further objective is to provide an implantable pacemaker with an integral cardiac condition classifier used to determine the level or degree of congestive heart failure in a patient.

Yet a further objective is to provide a method and device for classifying the cardiac condition of a patient which is more convenient than the methods using oxygen consumption.

Other objectives and advantages of the invention shall become apparent from the following description. As mentioned above, the condition of patients with congestive heart failure or cardiac impairment, is related to and is normally classified by their oxygen consumption during peak exercise levels. However, this same parameter, i.e., oxygen consumption is also related to certain metabolic demand parameters indicative of the hemodynamic demand during the exercise. One such parameter particularly suited for the present application is the minute volume. Typically, minute volume is obtained by measuring the transthoracic impedance measured across the pulmonary cavity during at least one complete breathing cycle.

More particularly, two values of interest are the peak MV, that is, the minute volume during peak exercise, and the rest MV, i.e., the value of MV during rest periods. The present invention takes advantage of the fact that the ratio of these two values can be used as an accurate indicia of the patient's condition.

In addition to MV, other physiological parameters may also be used to determine the classification of the patient. These parameters may include the QT interval or cardiac contractibility.

Briefly, a rate responsive pacemaker constructed in accordance with this invention includes an intrinsic sensor for sensing intrinsic events, a pace generator for generating pacing pulses on demand and a controller for generating commands for the pace generator. The pacemaker further includes a physiological demand sensor for sensing the metabolic demand of the patient. This demand is converted into a corresponding metabolic indicated pacing parameter, such as a pacing rate or pacing interval. This parameter and the sensed event are used by the controller to generate the pacing commands.

In addition, the pacemaker also includes an analyzer for analyzing the physiological demand. More particularly, this demand is monitored for a period of weeks and months to determine the levels of the physiological demand corresponding to various levels of physical activity. The variation in these levels is indicative of the classification of the degree of congestive heart failure in the patient. More specifically, the maximum and rest minute volume levels are determined and the ratio of these levels is used to generate a minute volume indicia. A preselected chart is then used to convert this indicia into a standard classification of the patient's congestive heart failure, said classification ranging from 0 for substantially no cardiac deficiency to a maximum of IV.

This ratio can also be used to limit the MAX rate allowed for the patient. Very low ratio indicates low MAX rate.

Once this classification is derived, it may be stored in a memory for downloading into a programmer in the future. In addition, the classification may be used by the controller to optimize the pacing regime for the pacemaker. In this manner, the pacemaker is automatically adapted to the level of CHF of the patient.

DETAILED DESCRIPTION OF THE INVENTION

Figure 1:
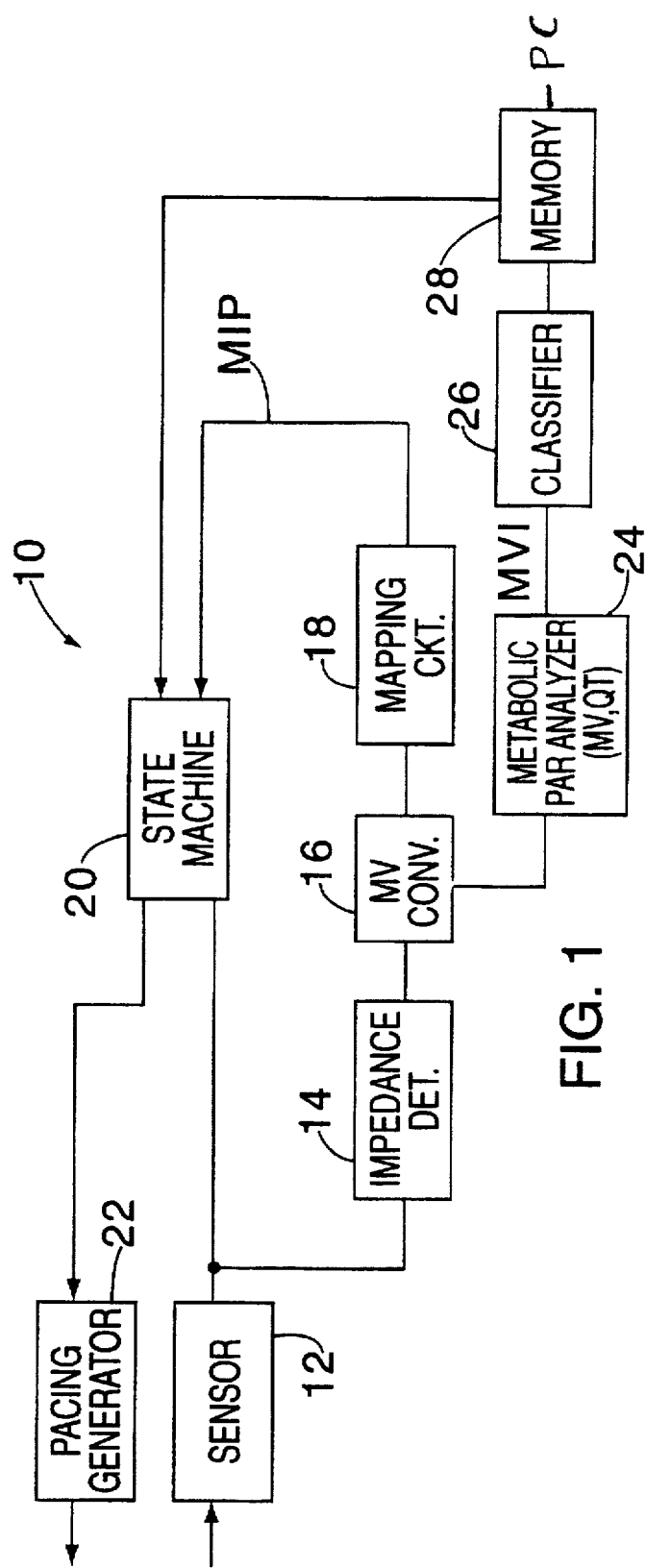
FIG. 1 shows a block diagram of a pacemaker constructed in accordance with this invention.

Referring first to FIG. 1, a pacemaker 10 constructed in accordance with this invention includes a cardiac sensor 12 for sensing intrinsic cardiac events and generating in response to cardiac sense signals. The pacemaker 10 further includes an impedance detector 14 for measuring the transthoracic impedance of the patient during at least one breathing cycle.

The impedance measured by detector 14 is converted into a minute volume by MV converter 16. It should be understood that other parameters may be used as well, such as the QT interval. The minute volume MV is used as metabolic demand parameter. This MV parameter is fed to a mapping circuit 18 which uses an RRF (rate response function) to generate in response to said MV parameter a metabolic indicated pacing parameter (MIP). This parameter MIP is fed to a state machine 20. The state machine 20 uses a preprogrammed set of rules to generate pacing commands on demand in response to the MIP parameter from mapping circuit 18 and the sensed signals from cardiac sensor 12. These commands are provided to a pacing generator 22 which in response generates pacing pulses. (For the sake of simplicity a single chamber operation is described, it being understood that normally pacemaker 10 operates in a dual chamber mode such as DDD or DDDR). A typical set of rules for the state machine for a DDDR mode is described in U.S. Pat. No. 5,441,523.

Importantly, the pacemaker 10 further includes a metabolic parameter analyzer 24 which analyzes the MV parameter to generate an MV indicia (MVI). This indicia is provided to a classifier 26 which generates a patient classification PC corresponding to the MVI.

Figure 2:
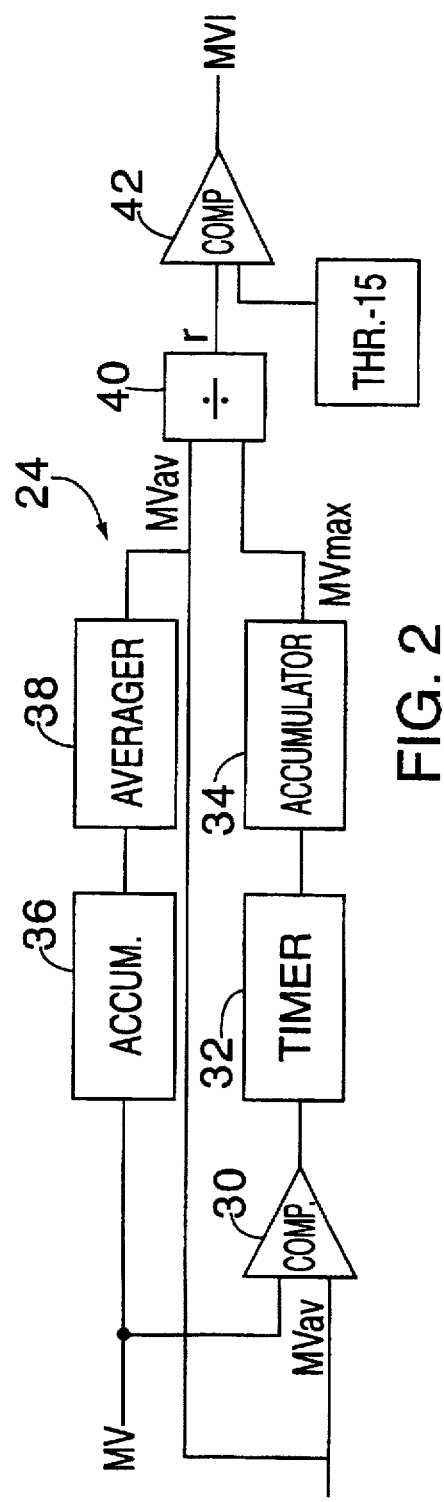
FIG. 2 shows details of a classifier circuit for the pacemaker of FIG. 1.

As shown in more detail in FIG. 2, the metabolic parameter analyzer 24 includes a comparator 30, a timer 32 and an accumulator 34. The analyzer further includes another accumulator 36 and an averager 38. The operation of the analyzer 24 is now described.

Figure 2A:
FIG. 2a shows typical heart rates at rest for patients of class 0–IV.
Figure 2B:
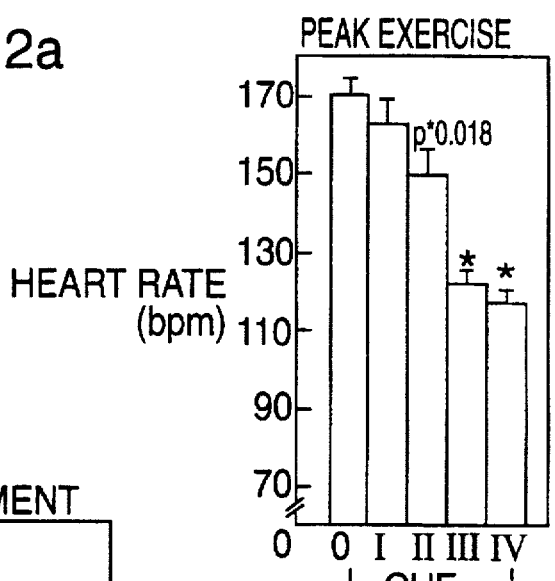
FIG. 2b shows typical heart rates at peak exercise for patients at class 0–IV.
Figure 2C:
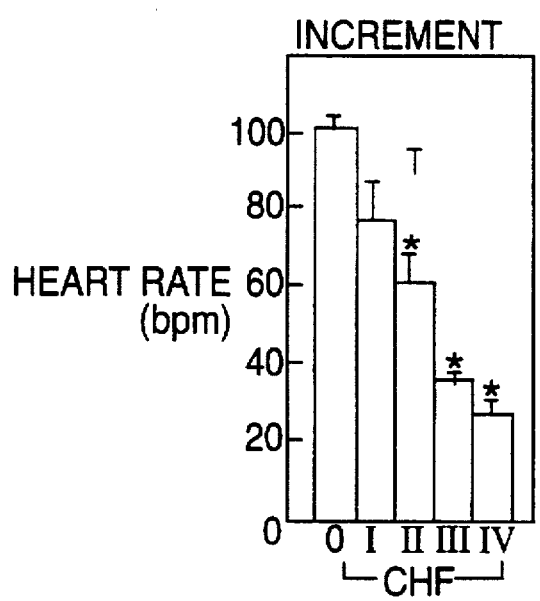
FIG. 2c shows incremental increase in heart rate from rest to peak exercise for patients of class 0–IV.

FIGS. 2a–2c show that, as the severity of CHF increases, the difference between the intrinsic heart rate from rest and peak exercise level decreases drastically.

Figure 3:
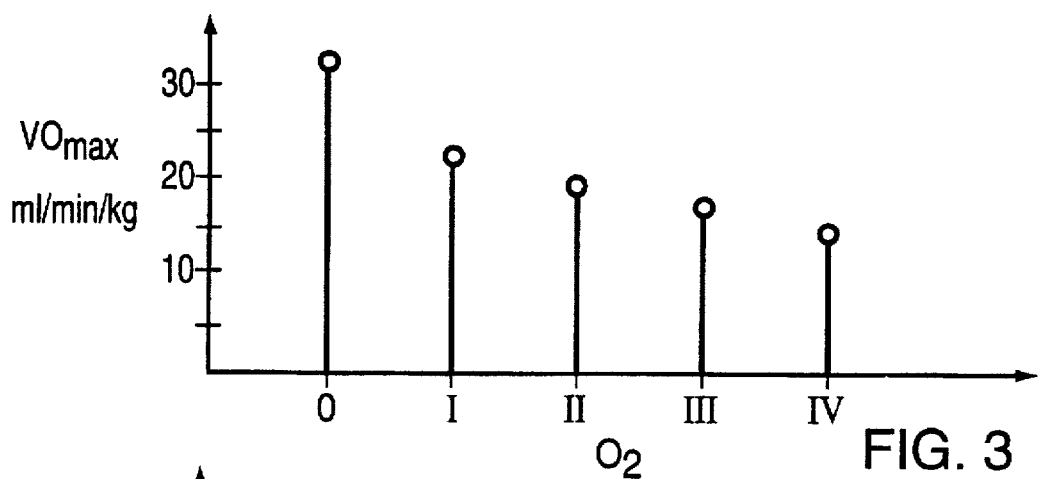
FIG. 3 shows graphically typical maximum oxygen consumption values of patients with different degrees of CHF.
Figure 4:
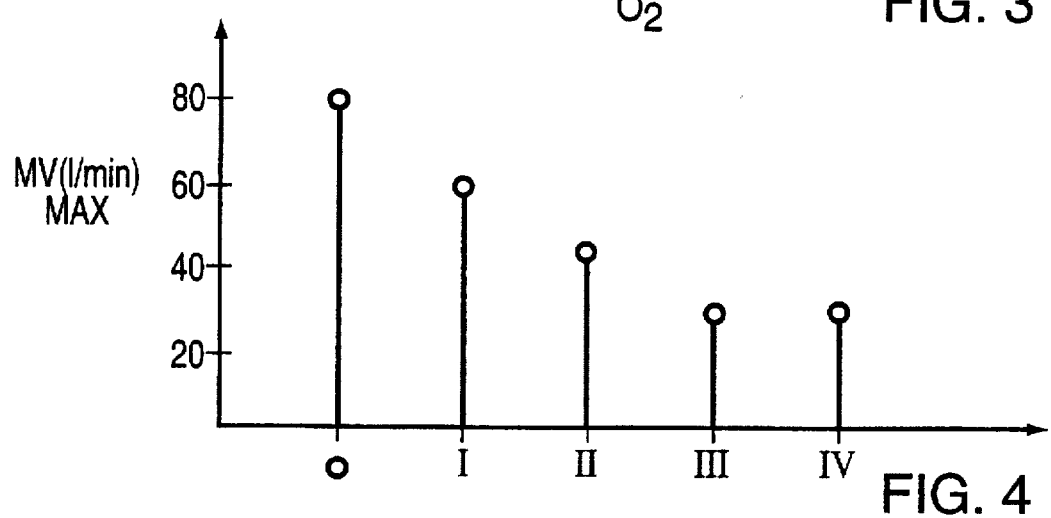
FIG. 4 shows graphically typical peak minute volume values of patients with various degrees of CHF.

The New York Heart Association defines CHF in terms of peak or maximum oxygen consumption during exercise, as shown in FIG. 3. As can be seen from this Figure, oxygen consumption falls drastically from Class 0 (no heart problem) to Class IV (severe CHF). Importantly, a similar graph for the maximum minute volume shown in FIG. 4 shows a very similar trend from Class 0 to Class IV. This comparison thus supports the validity of the basic premise of the invention, that is, that the heart condition of a patient may be determined from a physiological demand parameter such as the MV parameter. A further observation to be made, is that, as discussed above, and shown in FIGS. 2a, 2b, and 5, heart rate and the MV parameter at rest actually increases from patients with no cardiac problems (Class 0) to patients in Class IV. As a result, the ratio of the MV max to MV rest decreases drastically from about 10 for Class 0 to about 2 for Class IV. This phenomenon is exploited by the presented invention as follows.

Figure 5:
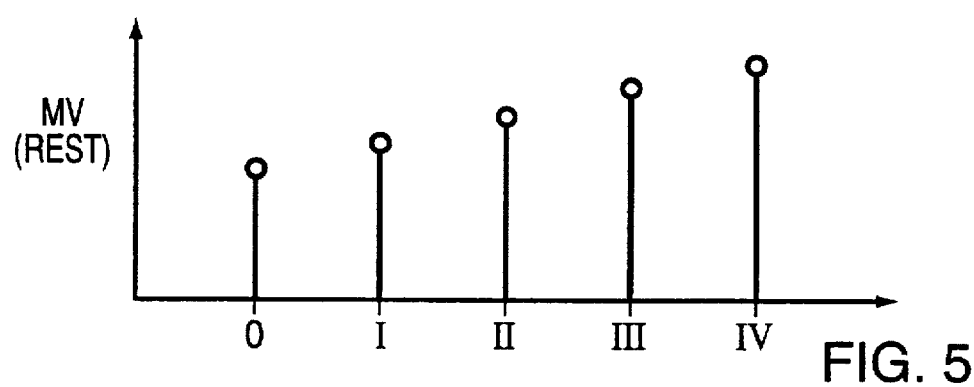
FIG. 5 shows graphically typical average minute volume values of patients with various degrees of CHF.

Referring to FIG. 2, the value of MV is sampled at regular intervals and stored in accumulator 36. This accumulator 36 accumulates the value of MV over a predetermined time period, such as, for example, a month. The value thus stored is averaged by an averager 38. Since everyone is most of the time at rest, the output of the average 38 is the MVavr value for the patient at rest. MVav (which is identical to the MV at rest) is shown in FIG. 5 for patients of various heart conditions.

The value MVav and the sampled MV is also fed to comparator 30. Comparator 30 is used to detect a rise in the instantaneous value of MV. The output of comparator 30 is fed to a 30 sec. timer 32 used to insure that a particular high MV episode lasts long enough to be considered a true rise and not just a transient phenomenon. If the timer finds that the MV stays high long enough, the high MV is fed to accumulator 34. This accumulator has the same time constant as the accumulator 36. Its output corresponds to the maximum MV (MVmax) for the patient, as charted in FIG. 4.

The two values, MVav and MVmax are fed to a divider 40 which divides, for example, MVmax by MVav. It is expected that the resultant ratio r may normally range from 1 to 12 or more. Another comparator 42 is used to insure that the ratio r does not exceed a preset threshold value, such as 15. If r is excessive, then it may be due to some anomaly and is ignored. However, if it is lower than 15, then an indicia MVI is generated which is equal to r. In other words:

For r≤15, MVI=r;

For r>15, MVI=0.

Figure 6:
FIG. 6 shows graphically expected values for the minute volume indicia generated by the circuit of FIG. 2 for patients with various degrees of CHF.

Returning to FIG. 1, the indicia MVI is fed to a classifier 26. The classifier 26 may be, for example, a look-up table. The classifier then uses the MVI indicia to assign to classification for the patient. One set of definitions for this purpose is illustrated in FIG. 6. According to this Figure, the classification of a patient PC is defined as follows:

| MVI | CLASSIFICATION (PC) |
|---|---|
| >10 | 0 |
| 6–10 | I |
| 4–6 | II |
| 3–4 | III |
| <3 | IV |

This classification PC is stored in a memory 28 for data logging, and later, downloading to a programmer. Optionally, this patient classification may also be provided to the state machine which in response may device to change its pacing rates. For example, one of the parameters used to derive an optimal pacing regime is the peak allowable pacing rate. Traditionally, an age-predicted heart rate is used for this maximum level using the formula:

*Pacing rate (max)=220−age (beats/minute).*

In the present invention, this formula is modified as:

*Pacing rate (max)=220−age−K (beats/minute)* where K=6 (10−MVI).

In the above description, the physiological characteristic used to determine the indicia was minute volume. Other physiological parameters may also be used, such as QT interval or cardiac contractility, and so on.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

I claim:

1. An implantable rate responsive pacemaker comprising:

a sensor for sensing intrinsic cardiac events and generating a corresponding sensed signal;

a pacing generator generating pacing signals in response to commands;

a metabolic demand sensor for sensing a physiological demand of the patient from a physiological characteristic, and generating in response a metabolic indicated pacing parameter;

a controller receiving said sensed signal and said metabolic indicated pacing parameter and generating said commands; and a classifier for generating an index indicative of a degree of congestive heart failure in said patient, said classifier including means for analyzing said physiological demand.

2. The pacemaker of claim 1 wherein said physiological demand corresponds to a peak oxygen consumption of said patient during exercise.

3. The pacemaker of claim 2 wherein said physiological demand is a minute volume.

4. The pacemaker of claim 3 wherein said analyzer includes a logic circuit for determining a variation in said minute volume responsive to different levels of physical activity, said index being related to said variation.

5. The pacemaker of claim 4 wherein said variation is a ratio between a peak minute volume corresponding to a peak exercise and a rest minute volume corresponding to resting.

6. A rate responsive implantable pacemaker comprising:

an intrinsic sensor for sensing intrinsic cardiac activity in a patient's heart, said intrinsic sensor generating in response sensed signals;

a pace generator for generating pacing signals in response to pacing commands;

a physiological sensor for sensing a metabolic demand of said patient based on a physiological characteristic of the patient;

a mapping circuit for mapping said metabolic demand into a corresponding metabolic pacing parameter;

a patient classifier for generating an indicia corresponding to a degree of congestive heart failure in a patient from said metabolic demand; and a controller receiving said sensed signals, said metabolic pacing parameter and generating said pacing commands.

7. The pacemaker of claim 6 wherein said controller receives said indicia and uses said indicia to generate said pacing commands.

8. The pacemaker of claim 6 further comprising a memory for storing said indicia.

9. The pacemaker of claim 6 wherein said physiological characteristic is one of minute volume, QT interval and cardiac contractibility.

10. The pacemaker of claim 6 wherein said physiological sensor senses a minute volume.

11. The pacemaker of claim 10 wherein said patient classifier includes an accumulator for collecting the minute volume levels corresponding to various levels of exercise by said patient.

12. The pacemaker of claim 11 wherein said classifier includes a first accumulator for accumulating a maximum minute volume corresponding to periods of maximum exercise and a second accumulator for accumulating a rest minute volume corresponding to periods of minimum exercise.

13. The pacemaker of claim 12 wherein said accumulators accumulate said minute volumes for extended time periods ranging in the order of 30 days.

14. The pacemaker of claim 12 wherein said classifier generates said indicia based on a variation of said maximum and rest minute volumes.

15. The pacemaker of claim 14 wherein said classifier generates said indicia as a function of a ratio of said maximum and rest minute volumes.

16. The pacemaker of claim 15 wherein said classifier includes a translator for translating said ratio into a corresponding patient classification.

17. A method of determining the CHF classification of a patient comprising the steps of:

measuring a physiological parameter related to the metabolic demand;

determining a variation of said parameter as a function of various levels of physical activity; and correlating said variation to a particular degree of classification.

18. The method of claim 17 wherein said step of measuring includes measuring a minute volume.

19. The method of claim 17 wherein said variation is a ratio between a high level physiological parameter corresponding to a high level exercise and a low level physiological parameter.

20. The method of claim 17 wherein said patient has an implant rate response pacemaker, said pacemaker including a metabolic sensor for sensing said physiological parameter and a controller for generating pacing pulses corresponding to said physiological parameter and another parameter comprising the step of generating said another parameter based on said degree of classification.

21. The method of claim 20 wherein said another parameter is a peak pacing rate.

* * * * *